United States Patent [19]

Silvus, Jr. et al.

[11] 4,352,983

[45] Oct. 5, 1982

[54] METHOD AND APPARATUS FOR MEASURING CONCENTRATION OF SUSPENDED OILS IN WATER

[75] Inventors: Howard S. Silvus, Jr.; Francis M. Newman, Jr.; Robert K. Swanson, all of San Antonio, Tex.

[73] Assignee: Southwest Research Institute, San Antonio, Tex.

[21] Appl. No.: 141,768

[22] Filed: Apr. 21, 1980

[51] Int. Cl.³ ............................................... G02B 5/16
[52] U.S. Cl. ..................................... 250/227; 356/70; 350/96.33
[58] Field of Search ................... 356/70; 250/227, 573; 350/96.29, 96.34, 96.33

[56] References Cited

U.S. PATENT DOCUMENTS 4,159,420  6/1979  Tsunoda .............................. 250/227
4,270,049  5/1981  Tanaka et al. ....................... 250/227

Primary Examiner—David C. Nelms
Assistant Examiner—Darwin R. Hostetter
Attorney, Agent, or Firm—Gunn, Lee & Jackson

[57] ABSTRACT

A method of quantitatively monitoring suspended oils in water combining the technologies of reversed-phase liquid chromatography and fiber optics is shown. A specially treated optical fiber collects and concentrates suspended oils on its surface so that optical transmission through the fiber is related to the contaminant concentration. The transmitted light from a treated optical fiber is detected by a photodiode and photocurrent is passed through an amplifier to give an electronic signal. The electronic signal is either recorded or indicated or generates a control signal whereby the light signal is translated into a value that corresponds to the concentration of oils suspended in water. To be sensed by the sensor cell, the fluid containing suspended oils is brought from a storage means to a reservoir and forced through the sensor cell by fluid pressure.

18 Claims, 7 Drawing Figures

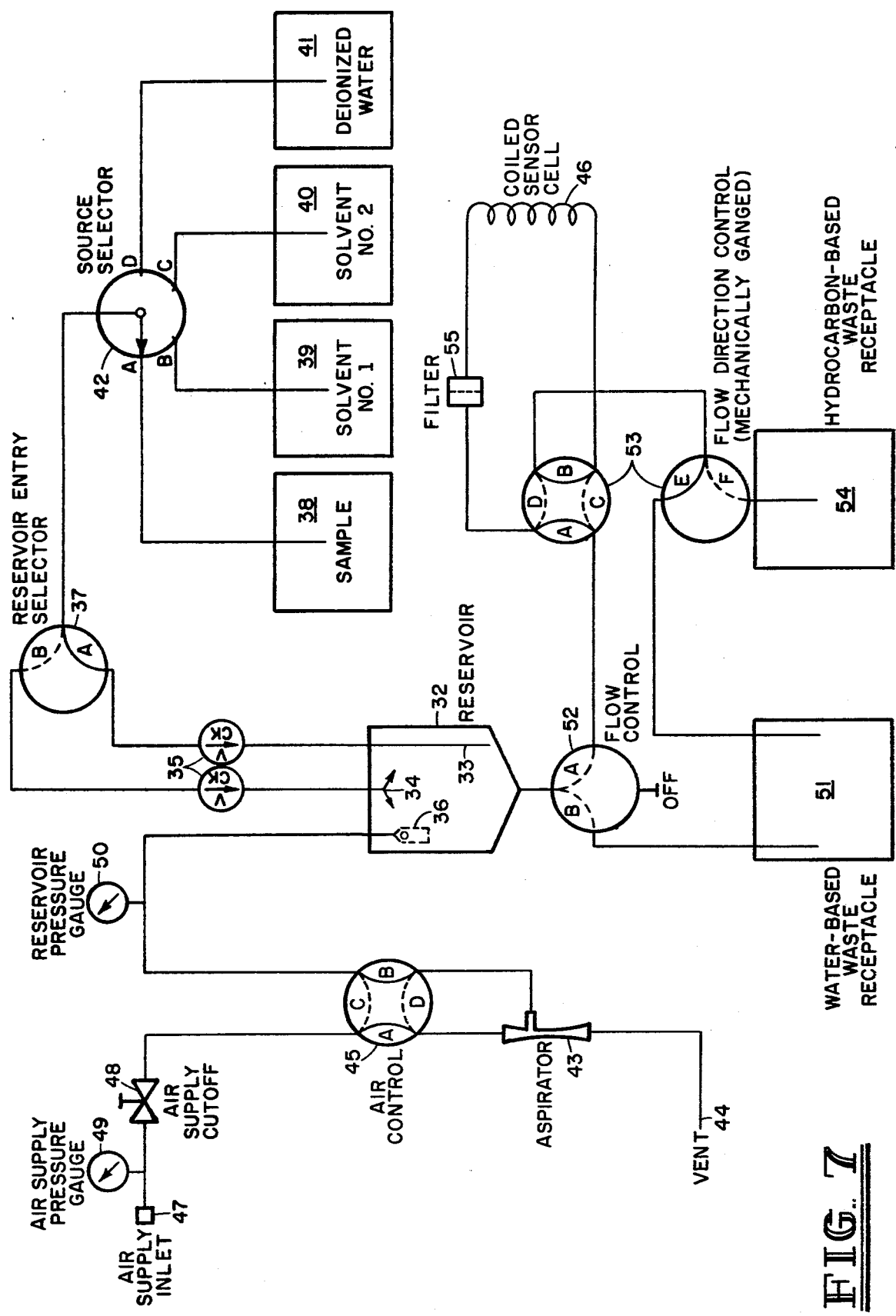

METHOD AND APPARATUS FOR MEASURING CONCENTRATION OF SUSPENDED OILS IN WATER

BACKGROUND OF THE INVENTION

This invention resulted from work done under Grant No. R804368-01 with the Environmental Protection Agency and is subject to the terms and provisions of said Grant.

Waste water or process water from such sources as refineries, shale-oil recovery plants, coal-conversion operations, chemical plants, ships, offshore drilling platforms, petroleum-handling facilities, and other industries may contain harmful quantities of hydrocarbon materials in suspension. Through programs coordinated and administered at the federal level, a significant effort is underway to eliminate or substantially reduce the quantity of hydrocarbon material discharged in waste water. Treatment processes which remove suspended hydrocarbons from waste water have been placed in service by many organizations cooperating in water pollution control. While installation and operation of such treatment processes are major steps toward elimination of hydrocarbon pollution, to achieve maximum effectiveness it is necessary to monitor the effluent of a waste-water treatment process to insure that the system is functioning correctly. A simple, inexpensive, automated, on-line instrument is needed for this important monitoring function.

Optical fibers usually have a central part or "core" surrounded by a tight-fitting sheath or "cladding". The cladding has a lower index of refraction than the core. Sometimes a protective jacket of plastic or other material is applied over the cladding to increase mechanical strength of the fiber and to make the fiber easier to handle. A light ray entering the core of the fiber within a cone defined by an acceptance angle strikes a boundary between the core and the cladding at an angle greater than the critical angle so that total internal reflection occurs. Total internal reflection is highly efficient, so such a ray is transmitted through the core with low attenuation by successive reflections at the core-cladding interface. The acceptance angle is a function of the indexes of refraction of (1) the core material, (2) the cladding material, and (3) the medium in which the fiber is immersed.

In the treated optical fiber oil-in-water monitor of the instant invention, an unclad optical fiber is used, that is, a fiber which has only a core and no cladding or protective jacket. The optical transmission properties of an unclad fiber are highly sensitive to the medium in which the fiber is immersed since that medium effectively functions as the fiber cladding. If the medium has a lower index of refraction than the core material, then light entering the fiber within the acceptance angle cone will be retained within the fiber by total internal reflection and will be transmitted with relatively low attenuation to the opposite end of the fiber. If, on the other hand, the surrounding medium has a greater index of refraction than the core material, then total internal reflection does not occur, and light entering one end of the fiber is rapidly dissipated into the medium.

Using the known characteristics and properties of optical fibers, a new approach to quantitatively monitoring suspended oils in water was conceived in which an oil-in-water monitor system employs a sensor cell through which a continuously flowing sample of the stream to be monitored is diverted. The sensor cell is similar to a reversed-phase liquid chromatographic column; however, in place of conventional column packing, the sensor cell contains a continuous unclad optical fiber, the surfaces of which have been made organophilic by chemical treatment, organophilic being defined as having an affinity for, attracting, adsorbing, or absorbing liquid organic matter. Suspended oil in the fluid flowing through the sensor cell is adsorbed on the optical fiber surfaces. Interaction between the light passing through the optical fiber and the oil adsorbed on the fiber surfaces produces a change in the through-transmission attenuation factor of the optical fiber. Rate of decrease in optical fiber transmission is related to the concentration of suspended hydrocarbons contaminating the stream being monitored.

The ultimate goal of developing the organophilic optical fiber oil-in-water monitor technique is to produce a reliable, simple-to-operate, easy-to-maintain and relatively inexpensive instrument for analysis of suspended hydrocarbons in water. Such an instrument could be employed in plants, on offshore platforms, aboard ships, or in other facilities which generate hydrocarbon polluted waste water to monitor the effectiveness of treatment systems or to determine the quantity of pollutant being discharged. In the future, availability of an economical instrument for monitoring suspended hydrocarbons in water should result in increased awareness of the quantity of hydrocarbon material being discharged into streams or other bodies of water. This awareness should, in turn, increase industrial concern with water treatment and pollution prevention. Thus, the ultimate impact and benefit of developing an analytical instrument employing the organophilic optical fiber technique should be a decrease in hydrocarbon pollution in areas where this problem is already severe and prevention of such pollution in new areas.

SUMMARY OF THE INVENTION

It is an object of the present invention to produce an inexpensive, reliable, easily operated and maintained instrument for analysis of suspended oils in water.

It is a further object of the present invention to provide a method of quantitatively measuring the concentration of suspended oils in water.

It is yet another object of the invention to provide an optical fiber that can be utilized to measure the concentration of suspended oils in water and also be incorporated into an instrument for analyzing suspended oils in water.

The term oil-in-water or oils-in-water used throughout the disclosure of the present invention is defined as a non-soluble organic liquid material suspended in water.

To accomplish the above objects, tests were performed to find an optical fiber that would be effective in measuring suspended oils in water and would also perform efficiently when used in an instrument for analyzing suspended oils in water. The unclad optical fiber of the invention, an organophilically treated optical fiber, has a greater index of refraction than water yet has a lower index of refraction than the oils to be detected. Such an optical fiber is very effective in analyzing water suspected of having suspended oils and is also useful in an instrument designed to monitor water possibly having suspended oils.

In operation, water containing suspended oils is passed over the treated optical fiber of the invention. Light is passed through the optical fiber. The transmitted light intensity, a function of the concentration of oils suspended in the water, is detected by a photodiode and translated into an electrical signal that is subsequently transmitted to an amplifier. The amplifier then produces an output signal which is easily interpreted and evaluated to determine the concentration of suspended oils in water. The oil suspension to be analyzed is conveyed from a stream being monitored or a storage receptacle to a sensor cell whereupon fluid pressure, perhaps from an air supply or a pumping device, forces the suspension into the sensor cell.

DESCRIPTION OF THE DRAWINGS

FIG. 7 is a flow diagram of one embodiment of the invention which has been tested.

DETAILED DESCRIPTION OF THE INVENTION

To provide for detection of oils suspended in water, an unclad optical fiber having a greater index of refraction than water, but at the same time having a lower index of refraction than the oils to be detected, is utilized. When such a fiber is in contact with water, it is effectively clad and transmits light from one end of the fiber to the other with low attenuation. However, when high refractive index oils deposit on the fiber surface, total internal reflection no longer occurs and some of the light propagating in the fiber is lost through the fiber walls. As the quantity of oil accumulated on the fiber surface increases, the internal reflection is further decreased and more light escapes into the medium, thereby reducing the intensity of the light arriving at the output end of the fiber. The degree to which total internal reflection is destroyed is related to the quantity of contaminant (i.e., thickness and extent of adsorbed layer) deposited on the fiber surface.

Figure 1:
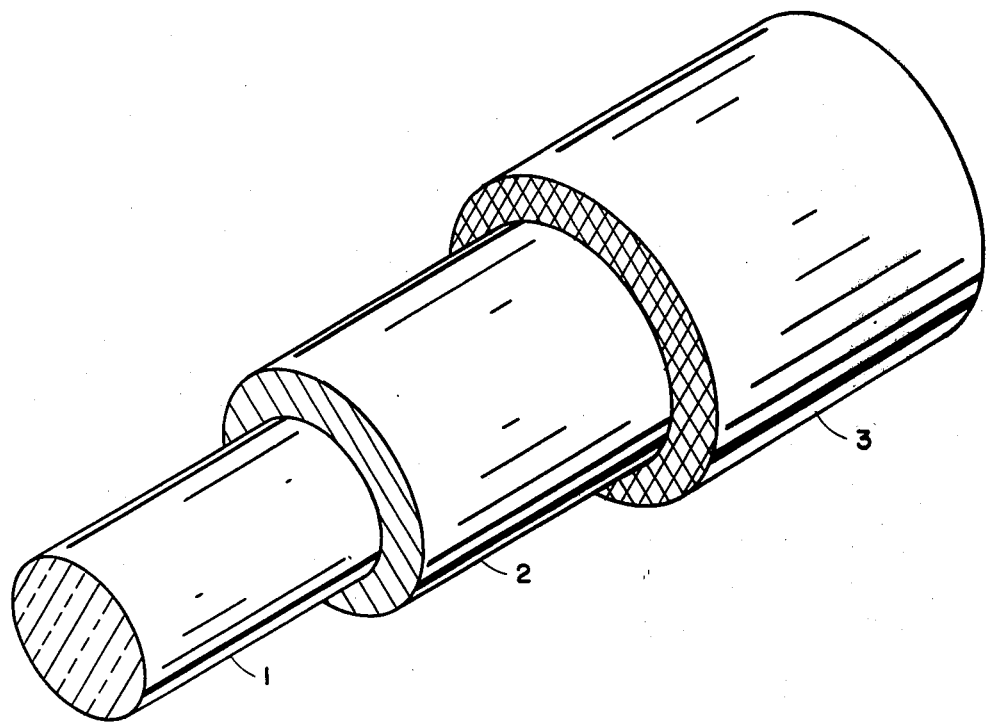
FIG. 1 is a perspective view of a typical optical fiber.

In FIG. 1 a perspective view of a typical optical fiber is shown. The core 1 is surrounded by a cladding 2. An optional protective jacket 3 encompasses the cladding to provide strength to the fiber. In the present invention, there is no protective jacket and the cladding is provided by the medium in which the optical fiber is immersed.

Figure 2:
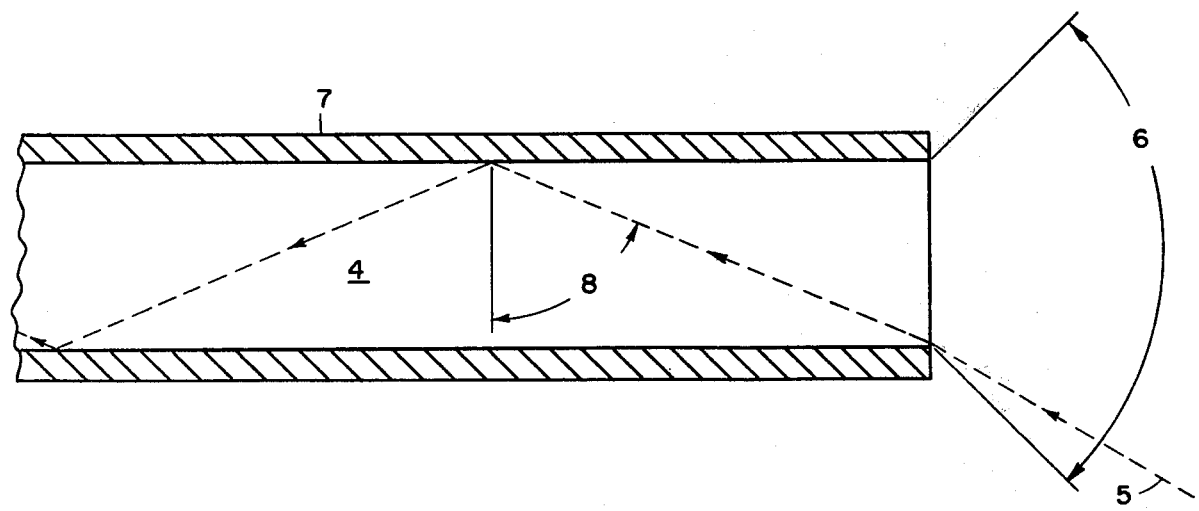
FIG. 2 is a longitudinal cross-sectional view of an optical fiber showing acceptance angle and incident ray path.

FIG. 2, a longitudinal cross-sectional view of an optical fiber, illustrates the concept of the present invention. An incident light ray 5 entering the core 4 of the optical fiber within a cone defined by the acceptance angle 6 strikes a boundary between the core 4 and the cladding 7 at an angle 8 greater than the critical angle so that total internal reflection occurs. The incident ray is thereby transmitted through the core by successive reflections at the core-cladding interface.

Converting this phenomenon into a useful analytical instrument, it is necessary to provide a constant-intensity light source at the input end of the fiber and a photosensor at the output end to convert light emitted from the fiber into a proportionate electrical signal. A flowing sample of the stream to be monitored is then passed over the optical fiber. If this stream contains only water with no oil contamination, then optical transmission through the fiber is unaffected. On the other hand, if there is oil contamination present in the water, optical transmission through the fiber will decrease at a rate which is related to contaminant concentration.

To maximize the above described effect, it is necessary to concentrate the available oil contaminant on the optical fiber surface. This function is provided by making the optical fiber surfaces organophilic (having an affinity for organic matter) by use of a chemical treatment process similar to that employed in preparation of column-packing materials for reversed-phase liquid chromatography. Such treatment chemically bonds organic functional groups to the fiber material.

Chemical treatment of optical fibers to render them organophilic was carried out by various methods. The most satisfactory method for purposes of the invention involved installing an optical fiber in a suitable length of capillary tubing coupled into the treatment apparatus. A reservoir was filled with a cleaning solution which was then forced through the capillary tube until the supply was exhausted. Rinsing solutions were passed through the system in a similar manner. The interior of the treatment apparatus was then dried by passage of heated gas through the tubing. Later, the silane treatment agent and subsequent rinsing solutions were forced through the apparatus. The interior of the treatment apparatus and fiber were again dried by passage of heated gas. To assist in overcoming heat loss through the metallic walls of the apparatus, the reservoir was wrapped with heating tape. In some coating treatments, hydrogen chloride by-product is produced. This by-product is scavenged, however, by tri-n-octyl amine which forms a toluene-soluble salt with the hydrogen chloride. Organosilane compounds determined to be suitable coatings agents for optical fibers included octadecyltrichlorosilane, octadecyltriethoxysilane, mixture of octadecyltriethoxysilane and octadecyltrichlorosilane, mixture of octadecyltriethoxysilane and trimethylchlorosilane, diphenyldichlorosilane, and n-decyltrichlorosilane.

It was experimentally determined that to function in a sensor cell an organophilic optical fiber should be curved to be highly active in attenuating transmitted light as oil collects on its surface. A multi-turn coil comprising an organophillically treated unclad optical fiber inside a metallic capillary tube possessed the desired characteristics to be useful in a sensor cell: increased active length, no optical cross-coupling between turns of the fiber coil, and increased contact between the flowing fluid and the fiber surface. By coiling the fiber-containing capillary tube, any desired active length could be achieved. Additionally, with the fiber contained inside an opaque tube, cross-coupling between turns of the coil was entirely eliminated.

A sensor cell found to be useful in the monitoring apparatus of the present invention comprised a coil of 1.59 mm (0.0625 in) O.D. by 0.58 mm (0.022 in.) I.D. stainless steel capillary tubing containing a 0.13 mm (0.005 in.) diameter optical fiber in its interior. Approximately 5% of the cross-sectional area of the capillary tube lumen was occupied by the optical fiber. The fluid sample to be tested was flowed through the capillary tubing so that it came in close contact with the fiber surface.

Figure 3:
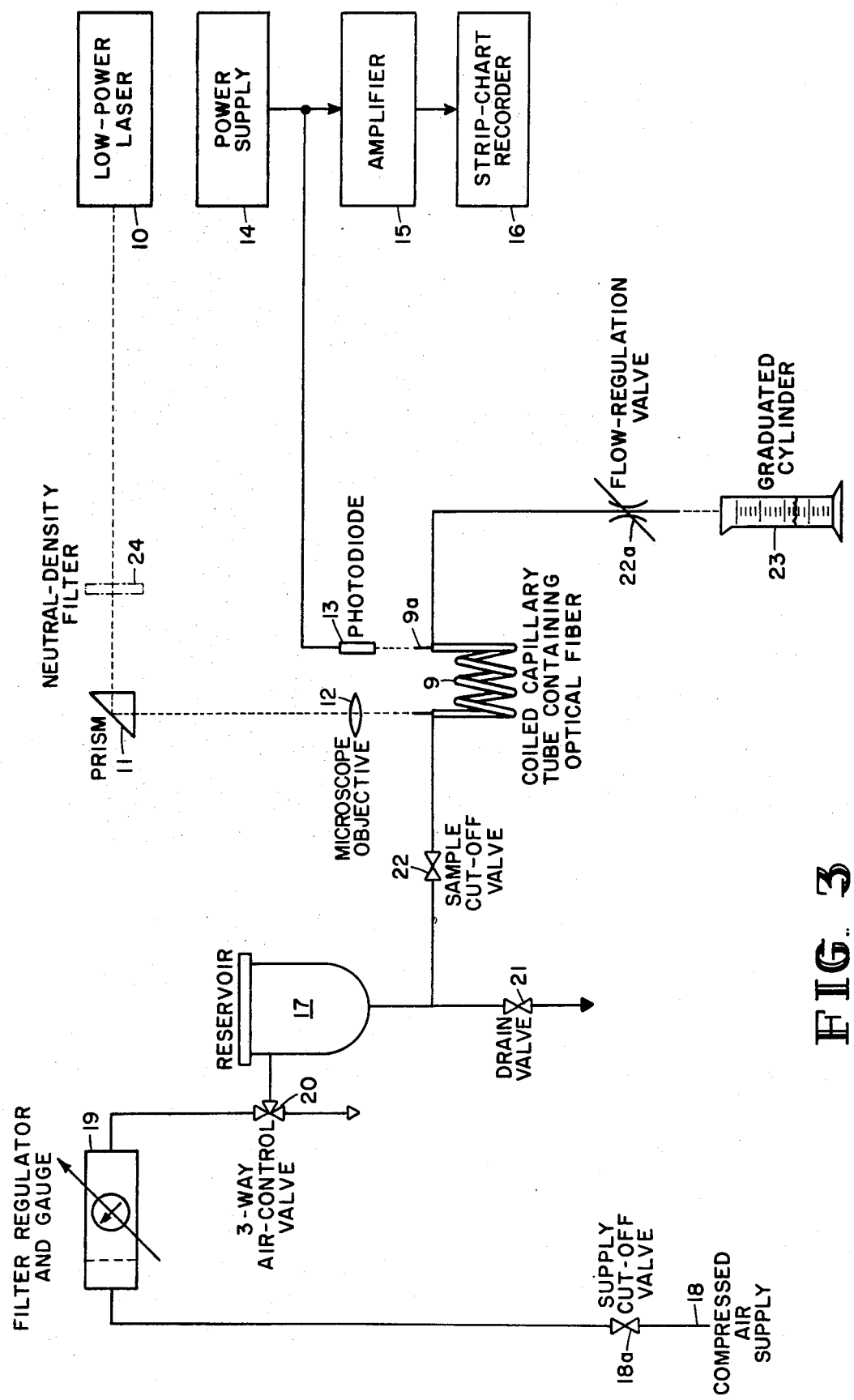
FIG. 3 is a pictorial schematic diagram of one embodiment of the invention.

To facilitate quantitative testing, the coiled capillary-tube sensor cell containing the optical fiber was installed in the test apparatus shown schematically in FIG. 3. The coiled capillary tube 9 containing optical fiber 9a was connected to the fluid handling apparatus by means of compression-type tube fittings, and the ends of the fiber were brought out through seals. The beam from a low-power helium-neon laser 10 was reflected by a 90° prism 11 through a microscope objective 12 and brought to focus on the input end of the organophilic optical fiber 9a under test. A neutral-density filter 24 could be positioned between the laser 10 and the prism 11. Optical energy emitted from the output end of the fiber was directed on the sensitive area of a silicon PIN (positive-intrinsic-negative) photodiode 13. A power supply 14 was provided to bias the photodiode, and an amplifier 15 was used to measure diode photocurrent. Amplifier output was recorded on a commercial strip-chart recorder 16 having logarithmic amplitude response.

A reservoir 17 was provided to contain the test fluid. Compressed air 18, obtained from a 700 kPa (100 psi) supply through a supply cut-off valve 18a and a filter-separator and pressure regulator 19 was admitted to the sealed reservoir above the liquid surface. Valve 20 provided for pressurizing and venting the reservoir, valve 21 provided for draining and flushing liquid from the reservoir, and valve 22 provided for controlling fluid flow through the capillary-tube sensor cell. Flow-regulation valve 22a enabled a constant flow rate to be maintained in the system and provided a back pressure to prevent bubbles from forming in the system. A graduated cylinder 23 was used to collect system effluent for the purpose of determining average flow rate. Tubing, fittings, valves, etc. in the fluid-flow path were made of 300 series stainless steel.

Test suspensions used to evaluate chemically treated fibers in the test apparatus were prepared using an ultrasonic disperser. A 1000-mg sample of the hydrocarbon contaminant to be used was added to 1 liter (L) of deionized water in a glass vessel. Cavitation produced by a high power ultrasonic horn broke the contaminant into very fine particles which remained suspended for several hours. Dilutions were made from the prepared stock to obtain a series of suspensions in half-decade steps of concentration (1000, 300, 100, etc. mg/L). Because contaminant concentrations greater than 1000 mg/L were beyond the range of primary interest, concentrations greater than this value were not prepared or used. The lowest concentration was either 10 mg/L or 1 mg/L depending upon the particular contaminant.

A list of the contaminants tested and their refractive indices is presented in Table I.

TABLE I

| CONTAMINANTS | REFRACTIVE INDEX |
| --- | --- |
| Heptadecylbenzene | 1.4798 |
| Dodecylbenzene | 1.4820 |
| n-Hexylbenzene | 1.4900 |
| t-Butylbenzene | 1.4927 |
| p-Xylene | 1.4958 |
| Ethylbenzene | 1.4959 |
| m-Xylene | 1.4972 |
| o-Xylene | 1.5055 |
| Chlorobenzene | 1.5241 |
| 2,6-Dimethylstyrene | 1.5315 |
| Cyclohexylbenzene | 1.5329 |
| 1,2,3,4-Tetrahydronaphthalene (Tetralin) | 1.5414 |
| Bromobenzene | 1.5597 |
| 3,3'-Dimethylbiphenyl | 1.5946 |
| Phenanthrene | 1.5973 |
| 1-Methylnaphthalene | 1.6170 |
| 1-Phenylnaphthalene | 1.6646 |
| Diesel Fuel | — |
| Crude Oil | — |

A chemically treated optical fiber 9a contained in a coiled stainless steel capillary tube 9 (hereinafter jointly referred to as the "sensor cell") was installed in the test apparatus. Typically, the stainless steel capillary tube 9 was approximately 0.8 m (31 in.) long and was formed into a 3.5-turn coil of 70-mm (2.8-in.) inside diameter. The ends of the optical fiber 9a projecting from the ends of the capillary tube 9 were threaded straight through the tee fittings of the test apparatus and were passed through silicone rubber compression seals which retained the test fluid in the sensor cell.

After sensor cell installation, the apparatus was cleaned with successive washes of approximately 150 ml each of acetone and methanol. Cleaning solvents and test suspensions were forced through the sensor cell by 300-kPa (44-psi) compressed air introduced into the reservoir. Following the two solvents, 300 ml of deionized water was forced through the sensor cell to insure that all solvent was flushed from the system; flow was terminated before all of the water had been used so that the flow path remained filled with deionized water.

Test suspensions of a particular oil contaminant in water were prepared in various concentrations as previously described. These test suspensions were introduced sequentially into the test apparatus reservoir beginning with the highest concentration. Each test suspension was forced through the sensor cell at a rate of approximately 0.5 ml/s until the fiber saturated or all of the test suspension was used. While the test suspension was flowing through the sensor cell, the amplified photodiode current was recorded on a strip-chart recorder. After use of each test suspension, the three-step clean-up procedure previously described was repeated. In most cases, this clean-up procedure restored optical transmission of the fiber to the value observed prior to introduction of any hydrocarbon contaminants.

Transmission loss occurring over a specified time interval was measured on the strip-chart record. This value of transmission loss in decibels (dB) was divided by the time interval in seconds (s) to obtain the slope of the line on the strip-chart record in units of decibels per second (dB/s). Slopes obtained with this procedure for a particular oil contaminant were plotted on logarithmic graph paper as a function of contaminant concentration. Typical curves are shown in FIGS. 4 and 5.

Figure 4:
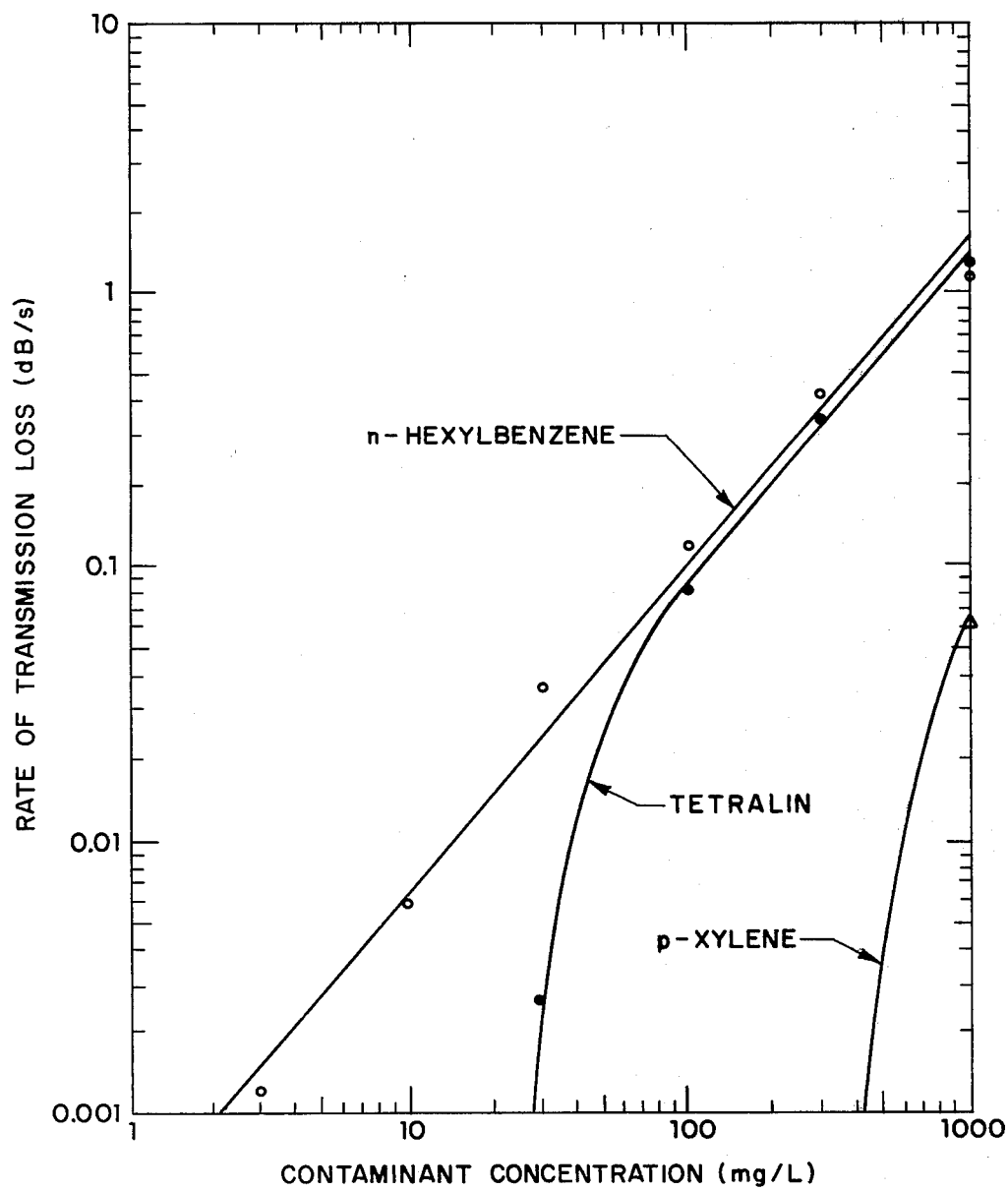
FIG. 4 is a graph of the response of a sensor cell to various contaminants in water.
Figure 5:
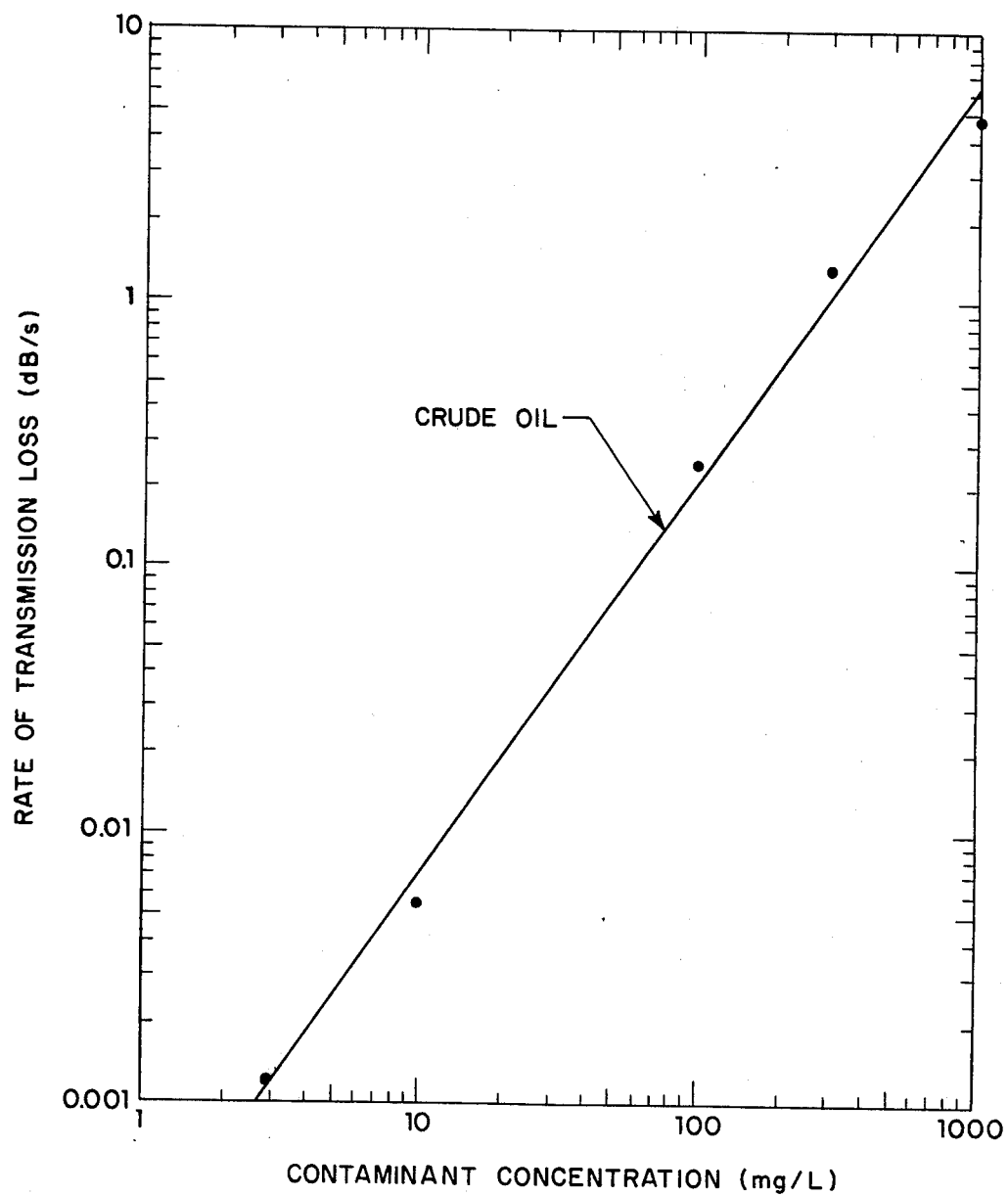
FIG. 5 is a graph of the response of a sensor cell to crude oil in water.

The curves of FIG. 4 illustrate sensor cell response to three contaminants: (1) n-hexylbenzene, (2) tetralin (1,2,3,4-tetrahydronaphthalene), and (3) p-xylene. The curve for tetralin is typical of the responses observed for many different contaminants; the curve is linear (on logarithmic coordinates) above a particular value of contaminant concentration (100 mg/L for tetralin) and falls off sharply below that value. The value of contaminant concentration at which system response (i.e., rate of transmission loss) is 0.001 dB/s is defined as the "detection threshold". From the curves in FIG. 4, the detection threshold for n-hexylbenzene is about 2 mg/L; for tetralin, approximately 30 mg/L; and for p-xylene, slightly greater than 400 mg/L. Data indicates that the response curve for tetralin is linear to a contaminant concentration of at least 7000 mg/L.

Although most tests of the organophilic optical fiber oil-in-water monitor system were conducted using pure hydrocarbon compounds, a few tests were conducted using diesel fuel and crude oil as the contaminant. The system was capable of detecting diesel fuel at a concentration of 17 mg/L. However, as illustrated in FIG. 5, the system was highly sensitive to crude oil and had a detection threshold of less than 3 mg/L.

Sensitivity (the derivative of the time rate of optical transmission change with respect to the contaminant concentration) and detection threshold vary from contaminant to contaminant. It appears from the data accumulated that detection threshold for a particular contaminant is related to the solubility of that compound in water. Although most hydrocarbon compounds which are less than 1% or 10,000 mg/Lsoluble in water are reported in the literature as "insoluble", some specific values of solubility in water at 25° C. were found for the contaminants listed below.

| 1-methylnaphthalene | 30 mg/L |
| m-xylene | 170 mg/L |
| o-xylene | 200 mg/L |
| p-xylene | 200 mg/L |
| ethylbenzene | 210 mg/L |

For these compounds, the detection threshold was slightly greater than the solubility figure as illustrated by the curve for p-xylene in FIG. 4.

Sensitivity of the coiled capillary-tube sensor cell containing an organophilic optical fiber treated with octadecyltrichlorosilane was not the same for all contaminants tested. This is illustrated in Table II for contaminants which had detection thresholds of 100 mg/L or less. Because sensitivity is not the same for all contaminants, it is necessary to calibrate the instrument in which the sensor cell is used for the particular contaminant or combination of contaminants expected.

TABLE II

SENSITIVITIES AND DETECTION THRESHOLDS OBSERVED FOR VARIOUS AROMATIC HYDROCARBON CONTAMINANTS

| CONTAMINANT | RELATIVE SENSITIVITY | APPROXIMATE DETECTION THRESHOLD (mg/L) |
| --- | --- | --- |
| n-Hexylbenzene | 1.00 | 2 |
| Cyclohexylbenzene | 0.48 | 10 |
| Heptadecylbenzene | 0.17 | 10 |
| 3,3'-Dimethylbiphenyl | 0.09 | 10 |
| 1-Phenylnaphthalene | 0.08 | 10 |
| 1,2,3,4-Tetrahydronaphthalene (Tetralin) | 0.80 | 30 |
| 1-Methylnaphthalene | 1.08 | 40 |
| 2,6-Dimethylstyrene | 0.08 | 40 |
| t-Butylbenzene | 0.09 | 40 |

The preferred coated reagent for use in the oil-in-water monitor instrument is octadecyltrichlorosilane. This agent produces the best overall response to a wide variety of oil contaminants. However, other coating agents as described above may be utilized when detection of a particular contaminant is desired.

Crown glass optical fibers having a refractive index of 1.5224 were utilized during early tests, but only a limited range of contaminants could be tested. Fused-silica optical fibers (refractive index 1.4585) used exclusively in later tests, were found to be the most useful since a wide range of oil contaminants could be used as discussed above.

In the test apparatus of the invention, a low-power helium-neon laser emitting red light at a wavelength of 632.8 nm was employed. A laser source was selected because it simplified coupling light into the input end of the optical fiber. However, there is no theoretical restriction on the type of light source. Comparison was made of the relative intensity of light emitted from the output end of an optical fiber when the input end was illuminated by four different light sources. The fiber used in these tests was similar to that used in the sensor cell, that is, fiber diameter was 0.13 mm (0.005 in.), fiber length was 1.0 m (39.4 in.) and fiber material was fused silica. Other suitable light sources are light-emitting diodes, infrared-emitting diodes, and incandescent lamps as well as lasers.

Because light emission from a laser is highly coherent, it appears to originate from an almost dimensionless point source. As a result, energy from the laser can be focused to a very small point approximating the diffraction limit. All of the other sources are relatively extended and, therefore, energy from these sources can not be focused to a very small spot. Since the input aperture of the optical fiber 9a was only 0.13 mm (0.005 in.) in diameter, capability of focusing a high percentage of the energy available from the source into a spot sufficiently small to enter the optical fiber aperture is extremely important. Even though some of the non-laser sources tested emitted sufficient energy to be useful, under the best conditions this energy can be focused to a spot no smaller than 1 mm (0.04 in.) and diameter; as a result, less than 2% of the available energy actually passed through the entrance aperture of the optical fiber 9a so that the source was very inefficiently utilized.

A prototype instrument incorporating the new sensor cell described above was assembled in the same manner as shown in FIG. 3. The cell employed a 0.13 mm (0.005 in.) diameter fused-silica optical fiber 9a 1 m (39 in.) long. The fiber was treated with octadecyltrichlorosilane while installed in a coiled stainless steel capillary tube 9 in accordance with the previously described process. Illumination for the optical fiber was provided by a 2-mW helium-neon laser 10 operating at the 632.8 nm (visible red) wavelength. The collimated beam from the laser was focused to a small spot by a 10X, 0.33 numerical aperture (N.A.) microscope objective 12. The objective lens was mounted in a 3-axis positioner to facilitate focusing and centering the small spot of light on the input end of the optical fiber. Light emitted from the output end of the optical fiber fell on the sensitive area of a PIN silicon photodiode 13. Ends of the optical fiber were cleaved using a sharp diamond scribe to initiate the break to produce a smooth, flat surface on the end of the fiber.

Figure 6:
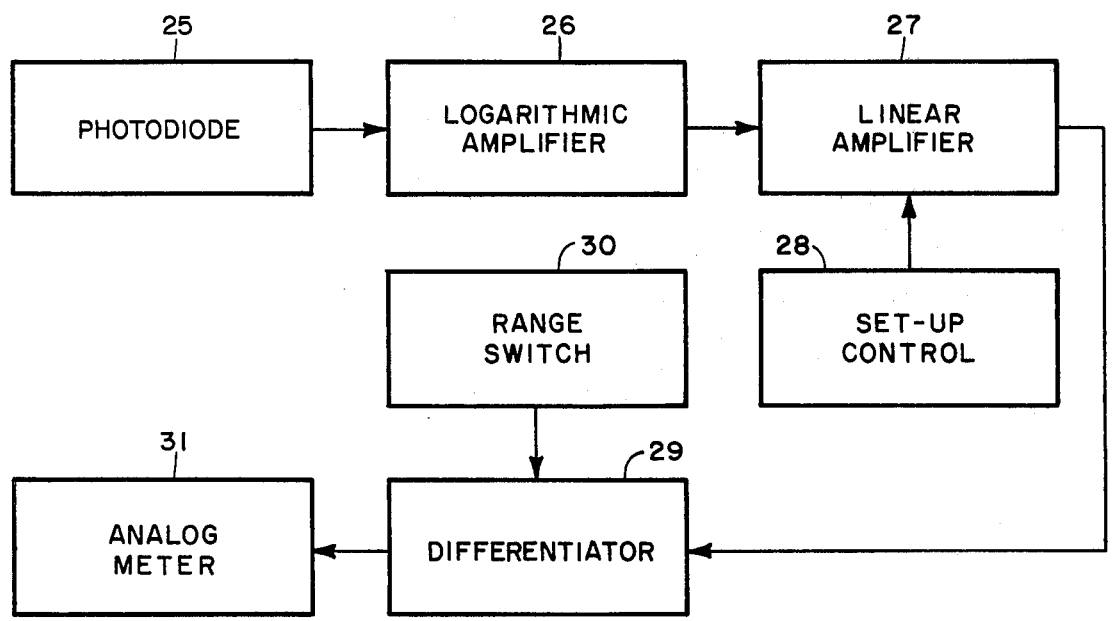
FIG. 6 is a block diagram of one embodiment of the signal processing system of the invention.

The signal processing system shown in block diagram form in FIG. 6 was devised to correlate the contaminant concentration and light intensity output. Output current of photodiode 25, which is linearly proportional to intensity of light emitted from the output end of the optical fiber, passes into a logarithmic amplifier 26 which delivers an output voltage proportional to the logarithm of the input current. The logarithmic signal is scaled and biased in a linear amplifier 27. The set-up control 28 establishes the initial parameters of the linear amplifier output voltage. Output voltage from this amplifier is impressed upon a differentiator 29 which delivers an output voltage proportional to the time rate of change of its input voltage. Time constant (i.e. gain factor) of the differentiator is set by means of a range switch 30 which facilitates selection of one of four full-scale sensitivity ranges. Differentiator output drives an analog meter 31 mounted on the front panel of the prototype instrument. The meter 31 is calibrated in units of decibels per second (dB/s) over the range from 0 to 1.0 dB/s, and the range switch provides multipliers of 0.01, 0.1, 1 and 10. System noise establishes a lower limit of 0.001 dB/s on the operating range of the system. In operation, two known concentrations of the contaminants to be analyzed are passed through the prototype instrument and scale readings are noted.

A flow diagram of the instrument is illustrated in FIG. 7. The central component of the fluid handling system is the reservoir 32 which is used for temporary storage of the sample and regeneration solvents. Materials may be introduced into the reservoir through a dip tube 33 which fills the reservoir smoothly from the bottom, or a spray nozzle 34 which directs the incoming material against the walls of the reservoir to improve cleaning action. Check valves 35 regulate the flow of material to the reservoir 32 and float valve 36 monitors the level of material in the reservoir 32. Entry path into the reservoir is determined by the reservoir entry selector 37, and the material entering the reservoir (i.e. Sample (38), Solvent No. 1 (39), Solvent No. 2 (40), or Deionized Water (41)) is determined by the source selector 42. Containers are provided for each of the four materials which can be admitted to the reservoir.

A compressed-air-operated aspirator 43 creates a partial vacuum in the reservoir 32, thus providing motive force for transferring fluids from their respective containers to the reservoir. The vent 44 relieves pressure. The air control 45 provides for directing compressed air into the aspirator during filling of the reservoir and into the reservoir for the purpose of forcing fluids through the coiled sensor cell 46. An air supply inlet 47 fitting and an air supply cutoff 48 are provided for convenience in handling the compressed air supply, and gauges are provided for monitoring air supply pressure and reservoir pressure, air supply pressure gauge 49 and reservoir pressure gauge 50, respectively.

Fluid flow from the reservoir can be cut off, directed into the sensor cell, or directed into the water-based waste receptacle 51 by the flow control 52. Direction of flow through the sensor cell is determined by the flow direction control 53 which incorporates two mechanically ganged valves. During analysis and flushing the sensor cell with deionized water, flow through the sensor cell 46 is in the forward direction, and waste fluid flows into the water-based waste receptacle 51. During regeneration, when either Solvent No. 1 or Solvent No. 2 is passing through the system, flow in the sensor cell 46 is in the reverse direction, and waste fluids are delivered to the hydrocarbon-based waste receptacle 54. A filter 55 in the forward-flow inlet side of the sensor cell 46 retains particular matter which could clog the cell. During regeneration, this filter 55 is back-flushed along with the sensor cell 46.

By using the treated optical fiber of the invention in an apparatus such as described and shown, suspended oils in water can be detected and their concentration can be determined.

We claim:

1. A method of quantitatively measuring the concentration of suspended oils in water comprising the following steps:
    passing light through an unclad optical fiber;
    treating said unclad optical fiber with hydrocarbon groups that are chemically attached to a surface of said unclad optical fiber by interatomic bonding to produce a surface which adsorbs very small quantities of said suspended oils and holds said suspended coils on said surface of said unclad optical fiber;
    contacting said unclad optical fiber with an oil-in-water suspension;
    detecting the light transmitted through the unclad optical fiber; and
    measuring the intensity of transmitted light, said transmitted light intensity being functionally related to the concentration of oils in suspension in water.

2. The method of claim 1 wherein said unclad optical fiber has a chemically bonded organophilic coating.

3. The method of claim 2 wherein said unclad optical fiber has a chemically bonded coating of an organosilane.

4. The method of claim 1 comprising an initial step of coating said unclad optical fiber including the following sub-steps:
    installing said unclad optical fiber in capillary tubing;
    forcing cleaning solution through said capillary tubing;
    rinsing said cleaning solution from said capillary tubing;
    drying said capillary tubing and unclad optical fiber contained therein by passing heated gas through said capillary tubing;
    passing silane treatment agent through said capillary tubing;
    rinsing said capillary tubing;
    drying said capillary tubing and unclad fiber contained therein to obtain said coated unclad optical fiber.

5. The method of claim 3 wherein said organosilane is selected from the group consisting of octadecyltrichlorosilane, octadecyltriethoxysilane, mixture of octadecyltriethoxysilane and octadecyltrichlorosilane, mixture of octadecyltriethoxysilane and trimethylchlorosilane, diphenyldichlorosilane, and n-decyltrichlorosilane.

6. The method of claim 1 wherein the light passing through said unclad optical fiber is from a laser.

7. The method of claim 1 wherein after measuring the concentration of a first suspension of oils in water and before measuring a second suspension of oils in water, said unclad optical fiber is cleaned.

8. The method of claim 7 wherein said cleaning of said unclad optical fiber comprises the following steps:
    forcing cleaning solvents around said unclad optical fiber; and
    flushing said cleaning solvents from said unclad optical fiber.

9. The method of claim 1 wherein prior to measuring the concentration of suspended oils in water known concentrations of oils suspended in water are measured for calibration.

10. An apparatus for quantitatively measuring the concentration of suspended oils in water, said apparatus comprising:

light means capable of concentrating a beam of light;

a treated unclad optical fiber receiving said beam of light at a first end thereof, said treated unclad optical fiber being treated so that hydrocarbon groups are chemically attached to sides thereof by interatomic bonding to produce sides which adsorb very small quantities of said suspended oils and hold said suspended oils on said side of said treated unclad optical fiber;

sensor cell encasing said treated unclad optical fiber to provide contact between suspension of oils in water and said sides of said treated unclad optical fiber;

light detector means for measuring intensity of light emitted from a second end of said treated unclad optical fiber and generating an output signal; and means responsive to said output signal for indicating variations in said light intensity.

11. The apparatus of claim 10 wherein said indicating means records said variations in said light intensity.

12. The apparatus of claim 10 wherein said indicating means controls a feedback loop.

13. The apparatus of claim 10 wherein said treated unclad optical fiber is encased in capillary tubing, said capillary tubing capable of having cleaning solutions, heated gas and treatment agent passed through to produce said treated unclad optical fiber in situ.

14. The apparatus of claim 10 wherein light means comprises a laser emitting said beam of light means into said first end of said treated unclad optical fiber.

15. The apparatus of claim 10 wherein said treated unclad optical fiber encased in said sensor cell is coiled.

16. The apparatus of claim 10 wherein said light detector means is a photodiode.

17. The apparatus of claim 10 wherein said suspended oils in water are delivered to said sensor cell by a fluid handling means.

18. The apparatus of claim 17 wherein said fluid handling means comprises:

multiple storage means for multiple fluids;

reservoir through which said multiple fluids from said multiple storage means may flow;

conveying means to carry said multiple fluids from said multiple storage means to said reservoir;

fluid selector means located between said multiple storage means and said reservoir for selecting the fluid to be conveyed;

air supply means connected to said reservoir for providing force to transfer said multiple fluids from said multiple storage means to said reservoir and through said sensor cell;

flow control means located between said reservoir and said sensor cell;

waste receptacle means connected to said flow control means.

* * * * *

UNITED STATES PATENT OFFICE
CERTIFICATE OF CORRECTION

Patent No. 4,352,983                    Dated  October 5, 1982

Inventor(s)  Howard S. Silvus, Jr.; Francis M. Newman, Jr.;
             Robert K. Swanson It is certified that error appears in the above-identified patent and that said Letters Patent are hereby corrected as shown below:

Column 4, Line 53:

"organophillically" should be "organophilically"

Column 7, Line 23:

"mg/Lsoluble" should be "mg/L soluble"

Column 9, Line 52:

"receptable" should be "receptacle"

Claim 1, Column 10, Line 15:

"coils" should be "oils".

Signed and Sealed this

Eighteenth Day of January 1983

[SEAL]

Attest:

Attesting Officer

GERALD J. MOSSINGHOFF

Commissioner of Patents and Trademarks